United States Patent [19]

Nehring

[11] 4,289,158
[45] Sep. 15, 1981

[54] SUCTION CONTROL APPARATUS

[75] Inventor: John R. Nehring, Woodcliff Lake, N.J.

[73] Assignee: C. R. Bard, Inc., Murry Hill, N.J.

[21] Appl. No.: 17,616

[22] Filed: Mar. 5, 1979

Related U.S. Application Data

[62] Division of Ser. No. 722,099, Sep. 10, 1976, abandoned.

[51] Int. Cl.³ .............................................. A61M 1/00
[52] U.S. Cl. .................................... 137/205; 128/276
[58] Field of Search ............... 137/205, 251, 853, 403, 137/406, 252

[56] References Cited

U.S. PATENT DOCUMENTS

| | | | |
|---|---|---|---|
| 2,636,507 | 4/1953 | Houghland | 137/252 |
| 3,286,741 | 11/1966 | Gellman | 137/853 X |
| 3,750,692 | 8/1973 | Tibbs | 137/205 |

Primary Examiner—Alan Cohan
Attorney, Agent, or Firm—Finnegan, Henderson, Farabow, Garrett & Dunner

[57] ABSTRACT

Disclosed is a chest drainage collection system including a manifold to which a suction control container, a water seal container, and one or more collection containers are releasably secured. The manifold includes a first passage communicating between the suction control and water seal containers and a second passage communicating between the water seal and collection containers. The system includes a suction control apparatus including means for reducing the loss of liquid in the suction control container due to entrainment in air and means for attenuating noise in the suction control container. A flexible plastic sleeve is provided for transmitting atmospheric air into an air chamber above the liquid in the suction control container without contact with the liquid in that container during the transmission.

21 Claims, 36 Drawing Figures

SUCTION CONTROL APPARATUS

This is a division of application Ser. No. 722,099, filed Sept. 10, 1976 now abandoned.

The present invention relates to a drainage collection system and particularly relates to a novel and improved closed drainage system for the pleural cavity.

Systems for draining gases and fluids from a patient's pleural cavity are currently used routinely. Probably the oldest, most commonly used and simplest drainage system, yet not devoid of difficulties and disadvantages as explained below, is the classic three-bottle closed drainage system. In that system, a suction control bottle, a water seal bottle, and a collection bottle are interconnected by tubes extending through stoppers in the bottle openings. A vacuum source is connected through the stopper of either the suction control bottle or the water seal bottle to maintain a negative pressure within the system. The suction control bottle carries a tube which extends a specified distance below the level of water in the suction control bottle. The depth of the tube in the suction control bottle controls the suction or negative pressure obtained in the system and in the pleural cavity. That is, the negative pressure in the system is a function of the head of water in the suction control bottle above the lower end of the suction control tube. In this classic three-bottle system, a tube from the collection bottle is connected with the patient's pleural cavity. Also, the lower end of the tube interconnecting the water seal bottle and the collection bottle extends slightly below the level of the water in the water seal bottle to form a water seal between the collection bottle and pleural cavity on one hand and the suction control bottle and vacuum source on the other hand.

When this system obtains a negative pressure exceeding the desired suction pressure, i.e. a high vacuum, atmospheric air flows through the suction control tube and bubbles through the suction control water into the air space above the water in the suction control bottle to maintain the desired vacuum level in the system. As evident, this classical system is readily understood because its operation involves simple physical relationships easily observed during operation. Many difficulties and disadvantages, however, occur in using the classic three-bottle system. For example, there is the constant danger of breaking the bottles. Also, the bubbling of air through the water in the suction control bottle is noisy and frequently disturbing to the patient. Further, there are no safeguards to prevent high positive or negative pressures in the system or to eliminate or minimize the danger of loss of suction control through evaporation or entrainment of suction control water in the air bubbled through the water in the suction control bottle. Also, there is nothing in this classic three-bottle system to prevent high negative pressure in the collection bottle and the pleural cavity from causing loss of water in the water seal bottle and consequent loss of the water seal.

More current closed drainage systems have improved the safety and handling characteristics of the classic three-bottle system. However, concurrently with improved safety and handling, these current designs also increase the difficulty of understanding the operation of the system. That is, these systems provide apparatus which appears foreign or unrelated to the classic three-bottle system with the result that the technician or user of such current designs misconceives them as totally new concepts and pieces of equipment. This frequently frustrates proper use of the new equipment and leads to its abuse with possible serious consequences to the patient.

The present invention provides a closed drainage system, particularly for use in draining the pleural cavity, which minimizes or eliminates the foregoing and other disadvantages associated with prior closed drainage systems and provides a novel and improved closed drainage system having various advantages in construction, mode of operation and result in comparison with such prior systems. More particularly, the present invention provides novel and improved safety, handling and other features in a closed drainage system which is easily operated, understood and comprehended, similarly as the classic three-bottle system. For example, rather than providing an appearance of a totally new closed drainage system of great complexity, the present invention provides individual containers readily recognized as corresponding in arrangement and function to the individual bottles of the classical three-bottle system. These individual containers are secured to a manifold which integrally contains the necessary passages by which the containers intercommunicate one with the other to achieve a closed drainage system, the manifold and containers having the improved safety and handling characteristics described hereinafter.

More particularly, the present invention provides a manifold having individual stations for receiving the respective containers and discrete passages wholly within the manifold. The containers are preferably secured to the manifold and the passages provide intercommunication between the containers when secured to the manifold. For example, when such containers are secured to the manifold at their individual stations, the manifold has a first passage which communicates between the suction control container and the water seal container and a second passage communicating between the water seal container and the collection container. The manifold has a third passage for establishing communication between the collection chamber and the pleural cavity as well as a fourth passage for coupling either the suction control container or the water seal container to a vacuum control source. The manifold also has a fifth passage providing for control of the suction within the containers. Thus, the manifold serves to mechanically, pneumatically, and hydraulically interconnect the containers such that the system functions in principle like and has ready analogy to the classical three-bottle system.

The foregoing described arrangement provides improved handling characteristics in that the containers, manifold and interconnecting passages form a single unit in use yet the containers are releasably secured to the manifold. This enables separate cleaning and sterilization of the containers and manifold apart from one another for reuse or disposal of the containers or manifold as desired. Also, individual bottles interconnected only by tubes as well as the tubes themselves are eliminated. Thus, breakage of bottles and faulty or incorrect connection of the tubes to the bottles and other apparatus are avoided. The present system is compact, and has the appearance of a modern medical device, yet its operation and function is easily and readily understood by technicians trained in the use of the classical three-bottle system. The feeling of unfamiliarity and hesitancy usually experienced in the use of new equipment is thus eliminated.

One of the improved safety features of the closed drainage system of the present invention provides for minimization or elimination of water particle or vapor entrainment in the air which normally would bubble through the water in the suction control bottle of the classical three-bottle drainage system as well as minimization of evaporation of the suction control water. As will be appreciated, entrainment of water in the air in the system during bubbling or water evaporation leads to loss of water in the suction control container. Undesirable variation in the negative pressure in the system results and accurate suction control is lost. In the present invention, suction control is obtained as a function of the water head above the tip of the suction control tube in the suction control container similarly as in the classic three-bottle system but without air-water interfacing whereby entrainment of water in air or evaporation is avoided in providing the suction control.

To achieve this, a flexible sleeve envelops the suction control tube in the suction control container. The sleeve has an open end at an elevation above the level of water in the container. When the negative pressure in the system is equal to or less than the desired negative pressure determined by the depth of the lower end of the suction tube below the water level in the suction control container, the sleeve collapses and seals about the tube. When the negative pressure exceeds the desired negative pressure, the atmospheric air displaces the sleeve away from the tube enabling the air to enter the sleeve and rise within it and into the air space in the suction control container above the water level. Thus entrainment of water or vapor in the air as it enters the suction control container is eliminated.

In another form, the suction control tube is surrounded by a rigid sleeve which forms, with the tube, a confined water channel. A hood or shield is located above this channel. Air bubbles through the water within the confined channel into the air chamber above the water in the suction control container. The shield, however, deflects and returns the water entrained by the air bubbling through the confined water channel back into the suction control container thereby minimizing water loss and avoiding loss of suction control.

Another safety feature in the present invention provides an anti-positive pressure valve which prevents loss of suction control through efflux of suction control water through the suction control tube. High positive pressures may be caused in the system when air leaks into the pleural cavity in excess of the vacuum pump capacity. Also, the patient may cough or the suction tubing may become occluded. To prevent such high pressures, a valve is located to vent air at a predetermined positive pressure from the system before the water in the suction control container is forced out of the suction control tube.

A further safety feature of the present invention prevents high negative pressures within the system and which can result in the loss of water in the water seal container and consequent loss of the water seal. That is, high negative pressure in the system can cause the water in the water seal container to be siphoned into the collection container causing loss of the water seal. It will be appreciated that high negative pressure can be caused by transient over-evacuation of the system by oversetting of the vacuum control or partial or complete occlusion by secretions in the suction tubing. To prevent such high negative pressure, a check valve is provided in the passage communicating between the suction control container and the water seal container.

Accordingly, it is a primary object of the present invention to provide a novel and improved closed drainage system.

It is another object of the present invention to provide a novel and improved closed drainage system having improved safety and handling features.

It is still another object of the present invention to provide a novel and improved closed drainage system having improved safety and handling features but which is readily understood and functions in principle like and has ready analogy to classic three-bottle closed drainage systems.

It is a further object of the present invention to provide a novel and improved closed drainage system having improved safety features including prevention of water loss in the suction control container through entrainment of water and/or evaporation of water during suction control.

It is a still further object of the present invention to provide a novel and improved closed drainage system having safety valves which prevent development of predetermined positive and high negative pressures within the system.

It is a still further object of the present invention to provide a novel and improved closed drainage system which is simply operated, readily monitored and easily understood.

Additional objects and advantages of the invention will be set forth in part in the description which follows and in part will be obvious from the description or may be learned by practice of the present invention. The objects and advantages of the invention may be realized and attained by means of the instrumentalities and combinations particularly pointed out in the appended claims.

To achieve the foregoing objects and in accordance with the purpose of the present invention, as embodied and broadly described herein, a closed drainage system of the present invention includes apparatus comprising a manifold; first and second passages carried by the manifold; a plurality of discrete containers including a collection container, a seal container, and a suction control container; means for securing the containers and the manifold one to the other with the first passage providing communication between the suction control container and the seal container and the second passage providing communication between the seal container and the collection container; means carried by the manifold defining a third passage for communicating between the collection container and a source of fluid to be collected external to the apparatus; means carried by the manifold defining a fourth passage for communicating between one of the suction control container and the seal container and a source of air under pressure external to the apparatus; means carried by the apparatus and in the seal container for providing a fluid seal between the first passage and the second passage; and means carried by the apparatus for controlling the pressure within the containers including means defining a fifth passage for communicating atmospheric air external to the apparatus into the suction control container.

Preferably the manifold is elongated and the containers are aligned in longitudinally spaced locations relative to one another along the manifold. Also the containers are preferably releasably secured to the manifold, for example by threadedly coupling them to the manifold.

The accompanying drawings illustrate plural embodiments of the present invention and, together with the description, serve to explain the principles of the invention.

Reference will now be made in detail to the present preferred embodiment of the invention as well as to various embodiments thereof, examples of which are illustrated in the accompanying drawings.

Figure 1:
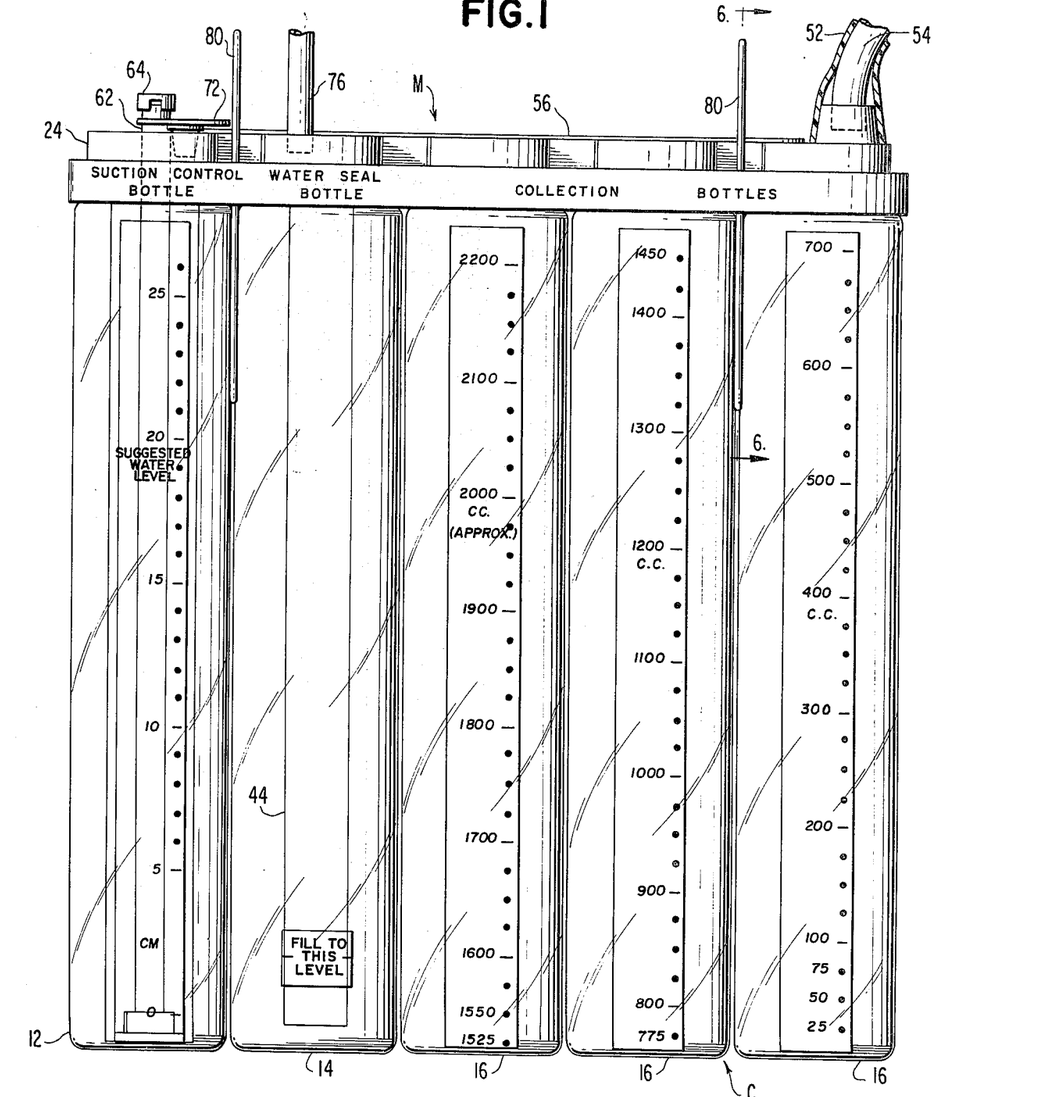
FIG. 1 is a side elevational view of a drainage collection system constructed in accordance with the present invention.
Figure 2:
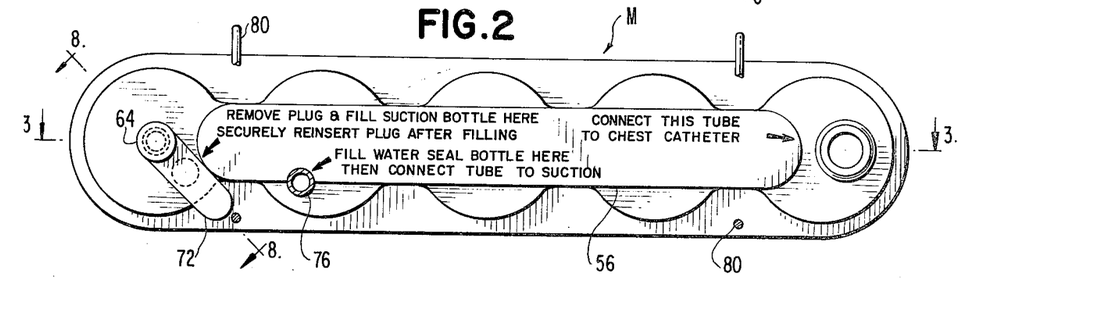
FIG. 2 is a top plan view thereof.
Figure 3:
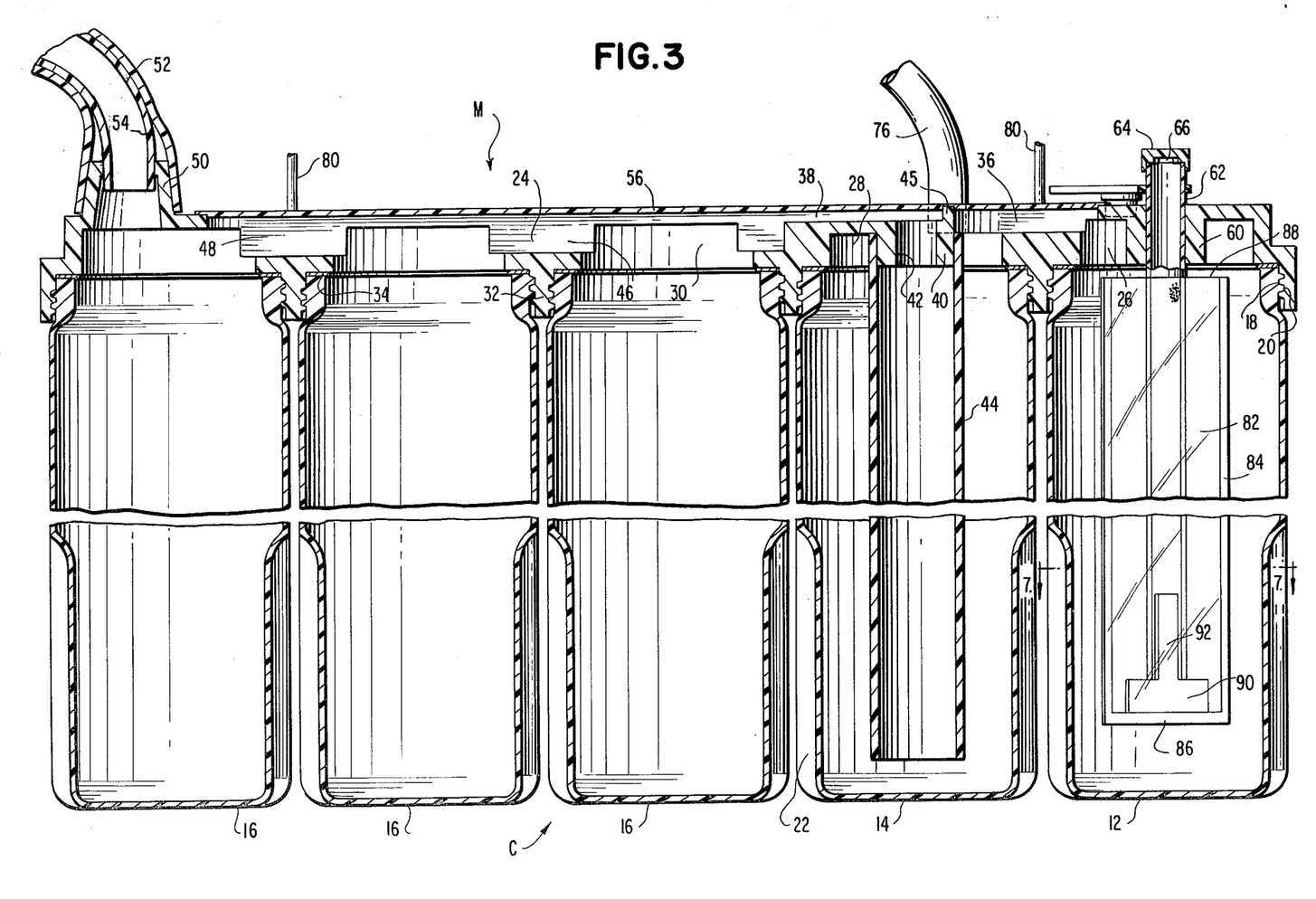
FIG. 3 is a cross-sectional view thereof taken generally about on line 3—3 in FIG. 2.
Figure 4:
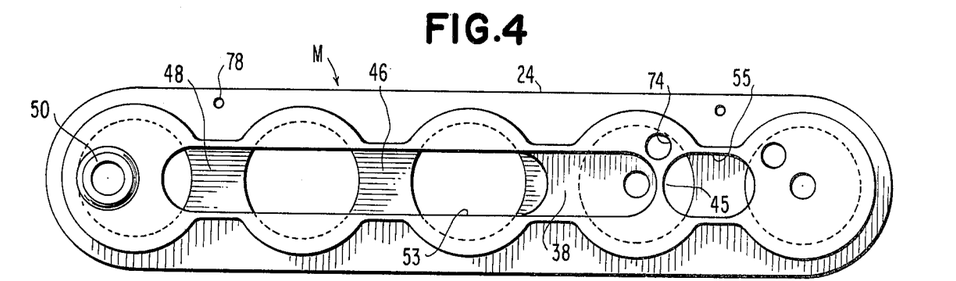
FIG. 4 is a top plan view of a manifold with its cover removed and which manifold forms part of the drainage collection system illustrated in FIG. 1.
Figure 5:
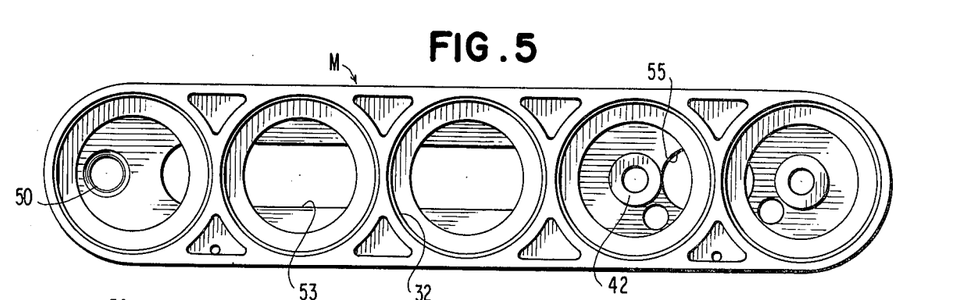
FIG. 5 is a bottom plan view of the manifold illustrated in FIG. 4.

Referring now to FIGS. 1–9 which illustrate a preferred embodiment of the present invention, and particularly to FIGS. 1–3, there is illustrated a drainage collection system constructed in accordance with the present invention including a manifold, generally designated M, and a plurality of longitudinally spaced and aligned containers, generally designated C, releasably coupled in a manner set forth below to the underside of manifold M. Containers C include a suction control container 12, a seal container 14, sometimes hereinafter referred to as a water seal container, and one or more collection containers 16. Each container C is generally cylindrical in shape having an open upper end terminating in a neck 18 which is externally threaded at 20 (FIG. 3), a closed lower end or bottom, and side walls which are recessed at 22 adjacent the container bottom to reinforce the container. The cross-sectional shape of the containers could be other than cylindrical, for example containers having square cross sections could be used to minimize space requirements for a given capacity unit. The containers C are preferably formed of a clear plastic material such as Lexan or an equivalent polycarbonate resin, to minimize breakage and weight. The containers C could, however, be formed of glass or other material if desired.

While the arrangement illustrated in FIG. 1 wherein the containers are longitudinally aligned in spaced relation one to the other along manifold M is preferred, it will be appreciated that containers C and consequently manifold M could be arranged otherwise, such as in a square construction provided the interconnections between the containers within the manifold and their connection externally of the device through manifold M, all as set forth below, are maintained in accordance with the function of the individual containers. Also, while the embodiment of FIGS. 1-9 utilizes five containers, three of which comprise collection containers 16, it will be appreciated that a fewer or larger number of collection containers could be utilized in lieu of the three collection containers illustrated. Further, where combination water seal and suction control containers are utilized, as hereinafter described in detail, one or more collection chambers could be utilized in conjunction therewith.

Figure 6:
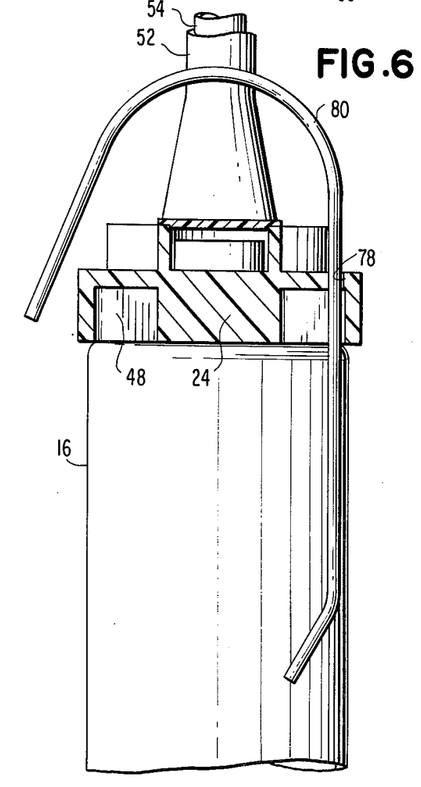
FIG. 6 is a fragmentary cross-sectional view of the drainage collection system taken generally about on line 6—6 in FIG. 1.

Manifold M is preferably formed of two parts including a header 24 and a cover 56. As best illustrated in FIGS. 3 and 6, the under or lower side of header 24 is provided with a plurality of longitudinally spaced and aligned stations to which the various containers C are preferably releasably secured. Particularly, manifold M carries at each station a depending internally threaded, circular, flange 32. Consequently, it will be appreciated that containers C are releasably secured to manifold M at the various stations by threading the container necks 18 to depending flanges 32. An annular seal 34 is disposed between the upper end of each container and manifold M before such securement to ensure sealing engagement between each container and Manifold M.

Inwardly of each manifold flange 32, there is provided a recess. More particularly, recesses 26 and 28 formed adjacent the right-hand end of manifold M inwardly on flanges 32 as illustrated in FIG. 3 lie in communication with suction control container 12 and water seal container 14 respectively when such containers are secured to manifold M. Similarly, recesses 30, spaced along the central and left-hand end portion of manifold M in FIG. 3, lie in communication with respective collection chambers 16 when the latter are secured to manifold M.

Manifold M also contains a plurality of internal passages communicating between the recesses. Particularly, manifold M includes a first passage 36 which communicates between the recesses 26 and 28 lying in communication with suction control container 12 and water seal container 14, respectively, when coupled to manifold M. A second passage 38 provides communication between the central collection chamber 16 and the water seal container 14 when secured to manifold M. Particularly, manifold M has a nipple 40 which depends into recess 28 and which nipple 40 has a bore 42 in communication with passages 38. A rigid sleeve 44 is secured to and depends from nipple 40 which, at its lower end, terminates short of the bottom of water seal container 14 for reasons discussed hereinafter. A wall portion 45 prevents direct intercommunication between passages 36 and 38. Additional passages 46 and 48 are provided in manifold M providing for communication serially between collection containers 16.

As best illustrated in FIG. 3, one end of manifold M has an upstanding nipple 50 to which is suitably attached a pair of concentric tubes 52 and 54. Tube 52 is utilized to secure the tube 54 to nipple 50. Inner tube 54 extends within nipple 50 in communication with the first of the serially connected collection containers 16. The opposite end of tube 54 is adapted for connection with the pleural cavity to be evacuated.

The passages 38, 46 and 48 open through the upper side of header 24 through an elongated slot 53 while passage 36 opens through the upper side of header 24 through a slot 55. A cover 56 overlies both slots 53 and 55 to close such passages and is suitably secured to header 24. Suction control container 12, water seal container 14, and collection containers 16 are thus in communication serially one with the other through such passages.

Figures 7, 8, 9:
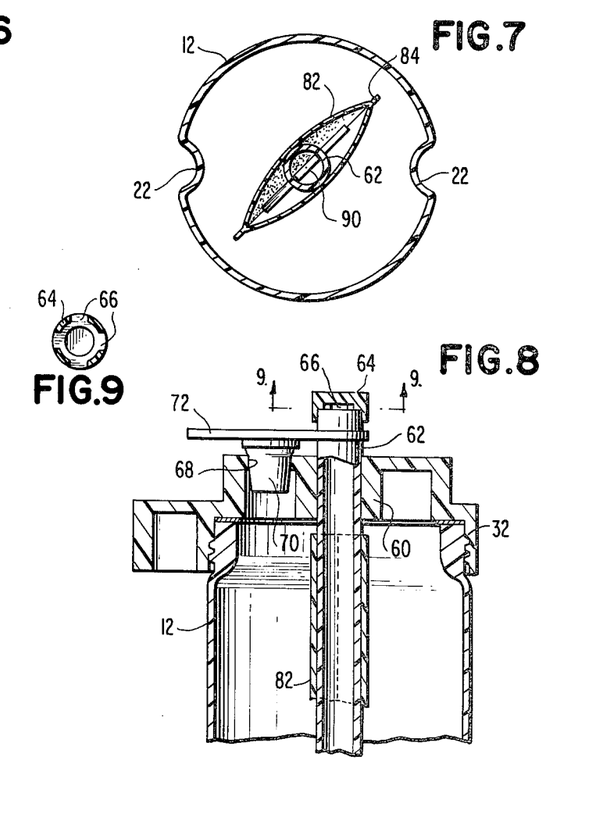
FIG. 7 is a cross-sectional view of a suction control container forming part of the drainage collection system hereof taken generally about on line 7-7 in FIG. 3.
FIG. 8 is a fragmentary cross-sectional view of the suction control container taken generally about on line 8—8 in FIG. 2.
FIG. 9 is a cross-sectional view of the underside of an adapter for use with the suction control container and taken generally about on line 9—9 in FIG. 8.

Turning now to FIGS. 3 and 8, header 24 is provided with a depending nipple 60 to which a tube 62 is rigidly secured. The upper end of tube 62 is provided with an adaptor 64. Adaptor 64 has lateral passages 66 (FIGS. 8, 9) which, when suitably seated on the upper end of tube 62, enable the passage in tube 62 to communicate freely with the atmosphere. Also provided through header 24 is an opening 68 which is normally closed by a plug 70. Plug 70 is carried on a tab 72, an end of which is rotatably coupled to the upper end of tube 62. Opening 68 is provided to enable suction control container 12 to be filled to the appropriate liquid level as discussed hereinafter.

Manifold M is provided with an opening 74 in communication with water seal container 14 when secured to manifold M. Opening 74 can be utilized to fill the water seal container 14 to the appropriate level as discussed hereinafter. A tube 76 is receivable within opening 74 when the apparatus is in use and connects with a source of suction, for example a vacuum pump, not shown. Manifold M is also provided with a pair of openings 78 adjacent its opposite ends and along one side of header 24 for receiving hangers 80 (FIG. 6) whereby the apparatus can be suitably hung from a support when in use. It will be appreciated from a review of FIGS. 1 and 2 that suitable indicia are provided on cover 56 and containers C containing instructions for use and that ancillary instructional material is not necessary.

Referring again to FIGS. 3 and 8, a pouch or flexible sleeve 82 is secured about the tube 62. Sleeve 82 is formed preferably of a flexible material, such as Tuftane, a urethane film, 2 mil thick type TF-310 manufactured by B. F. Goodrich Chemical Company, 299 Market Street, Saddlebrook, New Jersey. Sleeve 82 is preferably heat sealed along its sides and bottom 84 and 86, respectively, the top 88 being left open. Disposed in the lower end of tube 62 is a stand-off or inverted T-shaped member 90. The stem 92 of stand-off 90 is inserted into the lower end of tube 62 while the lateral extremities of the stand-off 90 extend beyond the diameter of tube 62. When sleeve 82 is disposed about tube 62, stand-off 90 prevents the lower portion of sleeve 82 from sealing about the lower end of tube 62. Sleeve 82 may be suitably secured about tube 62 for example by a suitable solvent.

In use, the apparatus may be provided with containers C secured to manifold M. If they are not, the containers are labelled and may be readily threadedly secured to the appropriate flanges of the manifold as indicated by the indicia on the manifold (FIG. 1). Water for the water seal bottle is provided to water seal container 14 through opening 74 to the level indicated on the side of container 14 (see FIG. 1). This level is above the lower end of tube 44 thus affording a water seal between the air chamber or space above the water in container 14 and the collection containers 16. The conduit 76 is then inserted into filler opening 74 and attached to a vacuum pump, not shown. Plug 70 is removed and water is additionally supplied to suction control container 12 through filler opening 68 to the desired level dependent upon the suction required. Suitable indicia is provided along the height of the suction control container and the desired suction in the system can be established by filling container 12 to the appropriate level. Once filled, plug 70 is reinserted into opening 68 to seal the system. Fluids other than water may be used in either container 12 or 14 but water is preferred due to its ready availability.

It will be appreciated that with tube 54 coupled to the cavity to be drained, i.e. a patient's pleural cavity, and tube 76 coupled to a suction or vacuum pump, not shown, suction pressure is provided in each container C through the serially connected passages 36, 38, 46 and 48, respectively, and to the cavity to be drained. When a negative pressure develops within the container 12 which exceeds the height of the water column between the lower end of tube 62 and the water level in suction control container 12, i.e. the water head above the lower end of tube 62, atmospheric air is admitted through passages 66 in adaptor 64, tube 62 and into sleeve 82. The air entering the lower end of sleeve 82 through tube 62 rises within sleeve 82 out of contact with the water in suction control container 12 and exits into the air space or chamber above the water level in suction container 12. When the negative pressure in container 12 is equal to or decreases below the desired negative pressure, flexible sleeve 82 collapses and seals about tubing 62 to maintain the vacuum level in the system at the desired negative pressure. Thus, air flowing into the suction control container cannot entrain any liquid particles or vapor during its passage into the suction control container since it does not contact the suction control water during such passage. Accordingly, the level of suction control water in the suction control container is maintained without loss due to air entrainment and the suction in the system is not therefore subject to variation by reason of any water loss whereby greater accuracy in controlling the suction applied to the cavity is achieved and maintained over extended periods of time.

Preferably, sleeve 82 is formed of thin highly flexible material which offers negligible resistance to collapse about sleeve 62 due to liquid pressure acting on it. With this type of material, sleeve 82 will seal about the tube until the vacuum in the system exceeds a negative pressure equivalent to the height of the liquid column defined between the lower end of suction control tube 62 and the liquid level in container 12, i.e. the water or fluid head above the lower end of suction control tube 62. Moreover, when the atmospheric air flows up sleeve 82, it causes sleeve 82 to flutter thereby affording visual evidence that the suction control system is working properly, and, in accordance with the present invention, without the danger of loss of suction control water as normally occurs by entrainment and evaporation in the prior class three-bottle drainage and other systems.

Figure 10:
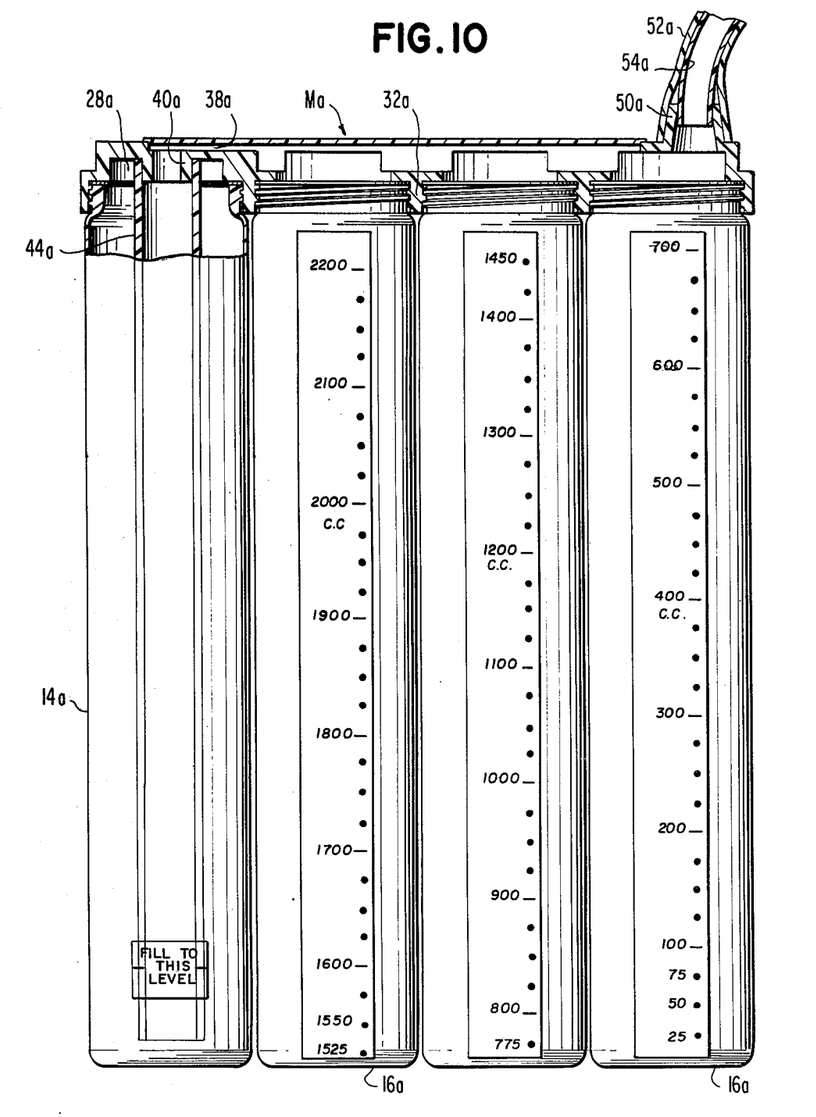
FIGS. 10 and 11 are views similar to FIGS. 1 and 2 respectively illustrating a gravity drainage system according to another embodiment of the present invention.
Figure 11:
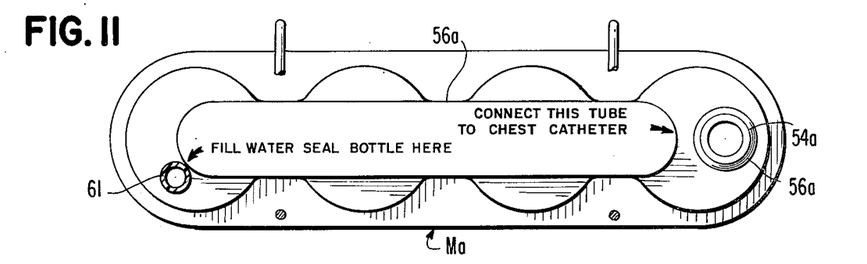

Referring now to FIGS. 10 and 11, there is illustrated a vacuum or gravity drainage system utilizing the principles of the present invention. This embodiment of the present invention is similar in many respects to the embodiment illustrated in FIGS. 1-9 and parts therein similar or identical in structure and/or function to parts in the embodiment of FIGS. 1-9 bear like reference characters followed by the suffix a. In FIGS. 10 and 11, the system constitutes a vacuum or gravity drainage system without a suction control container. Thus, the manifold Ma is formed similarly as the manifold M of the prior embodiment with the exception that the left-hand end of manifold Ma is closed and does not contain passages for use with a suction control container. In this form, however, a vent 61 is provided in manifold Ma in communication with the air chamber above the water level in the water seal container 14a. Vent 61 is preferably also provided with a filter such as cotton to prevent air borne contaminants from getting into the system when used for gravity drainage. Alternately, a flap or flutter valve can be used for this purpose. Vent 61 may be coupled to a vacuum source for vacuum drainage collection.

In use, this drainage system of FIGS. 10-11 functions similarly as the drainage collection system of the embodiment illustrated in FIGS. 1-9 except that external suction may or may not be applied. That is, the water seal container is filled to the appropriate level of the lower end of the water seal tube 44a and vent 61 is opened, if previously capped. The tube 52a is coupled to the patient's pleural cavity and fluids and gases flow therefrom by gravity or suction into the collection containers 16a.

Various further embodiments of the present invention are illustrated in FIGS. 12–36. These illustrations are schematic in nature. However, it will be appreciated that the various passages which interconnect the three types of containers are preferably formed integrally with the manifold as in the embodiment hereof illustrated in FIGS. 1-9, although discrete tubing interconnecting these containers and the system externally of the manifold, is sometimes illustrated and described and can be utilized. Also, like parts in function and/or structure as in the embodiment of FIGS. 1-9 are designated with like reference numerals followed by the letters a', b–v in the respective embodiments of FIGS. 12–36.

Figure 12:
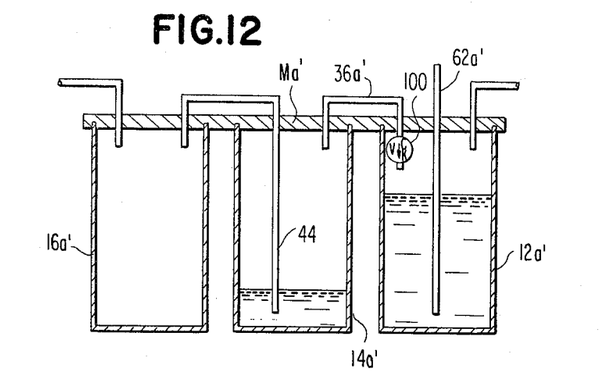
FIG. 12 is a schematic illustration of a further embodiment of the present invention.

Referring now to FIG. 12, there is schematically illustrated a drainage collection system having an anti-high negative pressure valve for preventing loss of the water seal. As will be appreciated, if the patient develops a high negative pressure within his pleural cavity or a high negative pressure is developed due to transient over-evacuation of the system by improper vacuum source setting or partial occlusion of the interconnecting passages and tubes, the water in the water seal chamber, unless prevented, may rise rapidly in water seal tube 44a and be siphoned into the liquid collection chambers 16a'. This would cause loss of the water seal both during and after the period of high negative pressure. To prevent loss of water seal, a check valve 100 is placed in the passage communicating between the water seal container 14 and suction control container 12. This check valve is illustrated at 100 in FIG. 12 in the passage 36a interconnecting suction control container 12a' and the water seal container 14a. Check valve 100 may comprise any suitable type permitting flow in a direction from water seal container 14a' to suction control container 12a' but preventing backflow from the latter to the former in the event of high negative pressure in the pleural cavity. The water within water seal tube 44a' will rise and fall to some extent notwithstanding check valve 100 but will rise insufficiently to permit transfer of water from water seal container 14a' to collection chambers 16a'.

Figure 13:
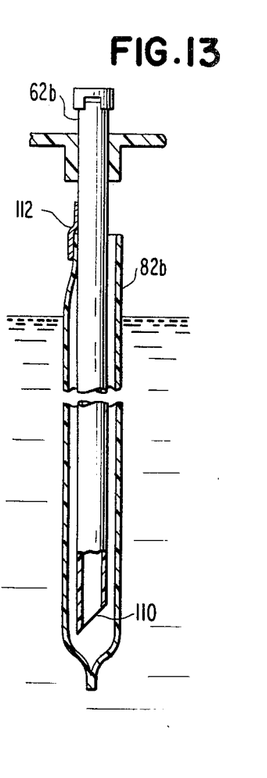
FIG. 13 is a fragmentary vertical cross-sectional view of a device for preventing entrainment of liquid in the suction control container during ingress of air in accordance with a further embodiment of the present invention.
Figure 14:
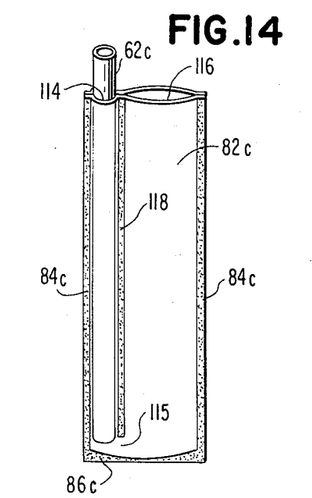
FIGS. 14 and 15 are perspective views of respective different embodiments of the device illustrated in FIG. 13.
Figure 15:
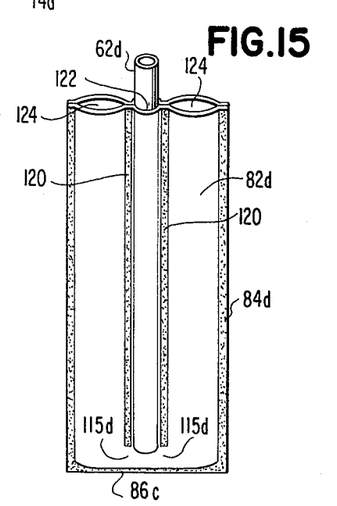

FIGS. 13, 14 and 15 illustrative variations of the pouch or flexible sleeve shown at 82 in the embodiment of FIGS. 1-9 hereof. Particularly, in FIG. 13, suction control tube 62b terminates at its lower end in a bevelled edge 110. The pouch or flexible sleeve 82b may be secured to the suction control tube 62b at the top of sleeve 82b by tape 112. Alternate forms of attachment of the sleeve 82b to tube 32b may be provided. For example, the tape 112 could be replaced by a tab with a hole formed through the tab for receiving the sleeve. Alternately, a hole can be provided in the sleeve wall near its upper open end for receiving the suction control tube. In both cases, an interference fit could be provided.

When the pressure in the system is equal to or less than the desired negative pressure, sleeve 82b collapses and seals about tube 62. When the negative pressure exceeds the water head, the atmospheric air enters tube 62b and rises within the sleeve 82b to the top of the suction control chamber. This rising air flutters the sleeve 82b and thus gives visual indication that the system it working properly.

In FIG. 14, sleeve 82c may be formed similarly as the sleeve 82 illustrated in FIG. 3. Additionally, however, two distinct passages 114 and 116 are formed. Preferably, opposite walls of sleeve 82c are heat sealed one to the other at 118 intermediate the sides of the sleeve which are heat sealed one to the other at 84c. This intermediate heat seal 118 extends close to, but is spaced from, the bottom heat seal 86c thereby forming a passageway 115 between passages 114 and 116. The passage 114 is formed to receive suction control tube 62c such that the lower end of tube 62c terminates short of the bottom 86c of sleeve 82c. Thus, passage 116 communicates with the lower end of suction control tube 62c through passageway 115 between intermediate seal 118 and bottom seal 86c. Sleeve 82c may be connected to suction control tube 62c by interference fit although any other suitable connection could be utilized. Also, sleeve 82c may be readily formed simply by sealing two flat pieces of thin wall plastic film together along their outer side edges and bottom and also intermediate the side heat seals as illustrated in FIG. 14.

In operating a drainage collection system using sleeve 82c, the water pressure seals the walls of the passage 116 to one another for pressures within the system equal to or less than the desired negative pressure. When the system pressure obtains a negative pressure greater than the desired negative pressure, the air entering tube 62c passes into and upwardly through passage 116 into the top of the suction control container. As in the prior embodiment, this passage of air does not trap or entrain water. It does, however, flutter the sleeve 82c to give visual indication of proper system operation.

FIG. 15 illustrates another embodiment of the pouch 82 constructed in accordance with the present invention. In this form, two flat pieces of thin wall plastic film are heat sealed one to the other along their opposite margins at 84d and along the bottom at 86c. Additionally, the opposite sides of the sleeve 82d are heat sealed along two vertically extending laterally spaced lines indicated 120 to define a central passage 122 flanked by passages 124. The intermediate heat seals 120 are spaced from the bottom seal 86 and thus define passageways 115d which communicate between the suction control tube 62d receivable within central passage 122 and the flanking passages 124. This embodiment functions similarly as the sleeve 82c of FIG. 14 except that instead of one passage there are two passages 122 and 124 for transmitting atmospheric air to the top of the suction control container and providing visual indication of proper system operation.

Figure 16:
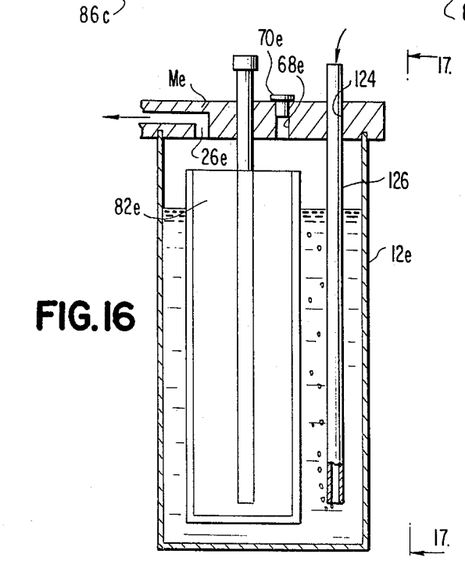
FIG. 16 is a vertical cross-sectional view of a still further form of a suction control container constructed in accordance with the present invention.
Figure 17:
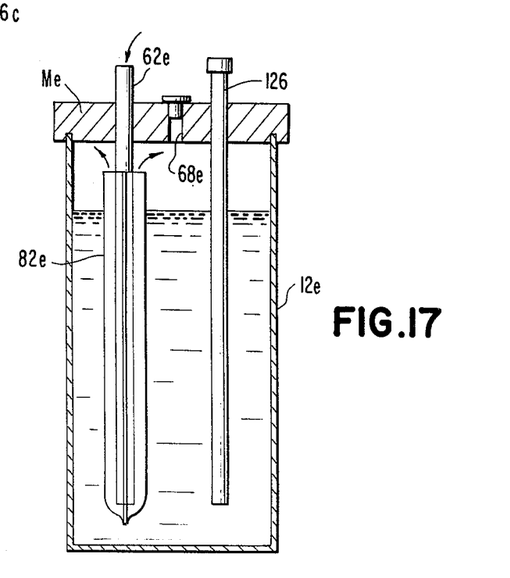
FIG. 17 is a cross-sectional view thereof taken generally about on line 17—17 in FIG. 16.

FIGS. 16 and 17 illustrate another embodiment of the present invention in which the user has the option of controlling suction quietly with visual indication of proper system operation or controlling the suction by bubbling air through water thereby providing both visual and audible indication of proper system operation. In this form, the manifold Me is provided with a suction control tube 62e, a filler opening 68e and plug 70e closing filling opening 68e, a passage 26e communicating with the water seal container, not shown, and a pouch or flexible sleeve 82e similarly as in the embodiment illustrated in FIGS. 1-9. In this form, however, manifold Me is also provided with another opening 124 in which is received a second suction control tube 126. Both tubes 62e and 126 extend into the suction control container 12e such that their lower ends terminate at like elevations.

If it is desired to avoid water entrainment, and loss of suction control water, as well as to provide for quiet operation with only visual indication of proper system operation, tube 126 is stoppered by suitable cap or plug, not shown, and the operation of the device proceeds as previously described. Visual indication of proper system operation is provided by the fluttering action of the sleeve 82e upon upward passage of air therethrough as previously discussed. If both visual and audible indication of proper system operation is desired, tube 62e is capped and tube 126 left open to the atmosphere. Atmospheric air will bubble through the water within suction control container 12e similarly as in the classic three-bottle system. Thus, the patient is given both audible and visual assurance that the system is functioning properly by the bubbling noise and through visual observation of the bubbles.

Figures 18, 19:
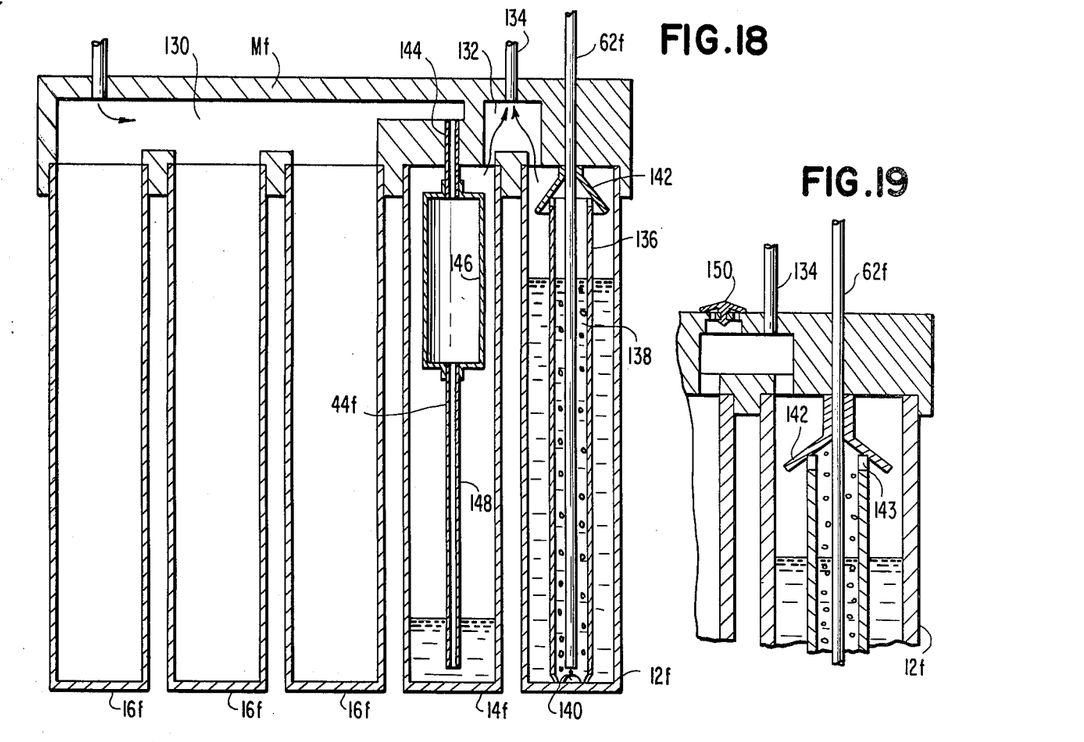
FIG. 18 is a vertical cross-sectional view of a further form of drainage collection system constructed in accordance with the present invention.
FIG. 19 is an enlarged fragmentary cross-sectional view illustrating the upper end of the suction control container of the drainage collection system illustrated in FIG. 18.

Referring now to the embodiment hereof illustrated in FIGS. 18 and 19, there is illustrated another form of drainage collection system for inhibiting suction control water loss as well as water seal water loss. Particularly, there is illustrated a drainage system comprised of a manifold Mf having hermetically sealed thereto a plurality of collection containers 16f, a water seal container 14f and a suction control container 12f. Passage 130 along the underside of manifold Mf provides for free communication between collection chambers 16f while a passage 132 provides communication between suction control container 12f and water seal container 14f. A conduit 134 communicates with passage 132 and is coupled to a source of suction, not shown.

Within the suction control container 12f, there is provided a suction control tube 62f surrounded by a concentric sleeve 136 which is radially spaced from tube 62f to define an annular chamber 138 therewith. The lower end of tube 136 is provided with openings 140 whereby the suction control water external to tube 136 is in free communication with annular chamber 138. As in the previous embodiments, suction control tube 62f terminates short of the bottom of the suction control container 12f and the water head above the lower end of tube 62f determines the suction pressure applied to the system. At the upper end of the suction control container 12f, there is provided a splash shield 142 including a frustoconical hood. The upper end of tube 136 has a plurality of openings 143 (FIG. 19) whereby the air space in annular chamber 138 above the liquid level therein lies in free communication with the air space above the liquid level in suction control container 12f.

In water seal container 14f, there is provided a water seal tube 44f including an upper section 144 in communication with passage 130, a diametrically enlarged generally tubular intermediate section 146 and a diametrically reduced lower section 148 which terminates below the level of water seal container 14f.

The operation of the drainage collection system according to this embodiment is similar to the operation of the embodiment disclosed in FIGS. 1-9 hereof except with respect to the apparatus for preventing entrainment of water in the air in the suction control chamber and for preventing loss of water seal. Particularly, when the pressure within the system exceeds a predetermined negative pressure, atmospheric air entering suction control tube 62f bubbles upwardly in the annular space 138. The annular space 138 thus confines the bubbles which impinge against the underside of the splash shield 142. Shield 142 directs the water entrained in the air bubbles downwardly outside the bubble confining tube 136 for return to the water within suction control container 12f. In this manner, water and vapor loss in the suction control container is minimized and, to a very significant extent, water lost through entrainment with the air bubbles is returned by use of the bubble confining tube 136 and splash shield 142.

The intermediate section 146 of water seal tube 44f in the water seal container 14f prevents loss of the water seal water by reflux of water into the collection chambers. For example, when the patient's pleural cavity develops a high negative pressure water could undesirably flow from the water seal container 14f through the water seal tube 44f into the collection chambers with ultimate loss of water and consequent loss of water seal in the water seal container 12f. The enlarged intermediate section 146 prevents such water loss by providing an enlarged volume into which the water in the water seal container 14f may flow before flowing into the collection containers 16f. That is, in the event of high negative pressure in the pleural cavity, water seal water flows into the enlarged volume 146 until the lower end of the water seal tube is exposed and the vacuum broken. Once this occurs, water in the enlarged volume 146 flows back into water seal container 14f.

In FIG. 19, there is provided a positive pressure relief valve 150 in communication with passage 132 and preferably formed of an elastomeric material overlying openings to the atmosphere formed in the manifold wall. This positive pressure within the system and serves as a pressure relief for such positive pressures. For example, valve 150 may open under 1 to 2 inches of water pressure but remains closed for pressures less than that. This positive pressure relief may prevent lung collapse and loss of suction control water.

Figure 20:
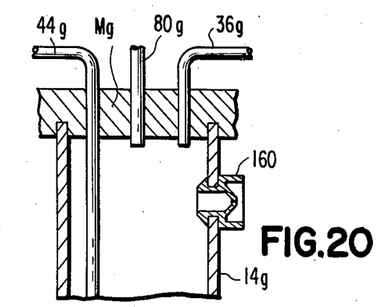
FIG. 20 is a vertical fragmentary cross-sectional view illustrating a valve structure to prevent positive pressure in the system.
Figure 21:
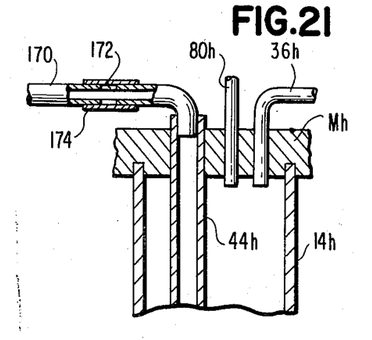
FIG. 21 is a view similar to FIG. 20 illustrating a further form of valve for preventing positive pressure in the system.
Figure 22:
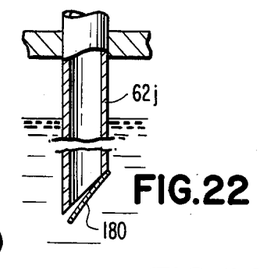
FIGS. 22 and 23 are vertical cross-sectional views illustrating the lower ends of the water seal tube and suction control tube respectively and valves associated therewith.

Referring now to FIGS. 20, 21 and 22, there is illustrated various means for preventing development of a predetermined positive pressure in the system. This positive pressure could occur when air leakage into the patient's pleural cavity exceeds pump capacity or when the patient coughs or when the suction tubing to the vacuum source is partially or fully occluded. In FIG. 20 there is illustrated an anti-positive pressure check valve 160 provided in the wall of water seal container 14g. Valve 160 is preferably formed of a molded one piece elastomeric material. As in previous embodiments, water seal tube 44g, a tube 80g for connection with the suction pump, not shown, and a passage 36g for connection to the suction control container are provided through manifold Mg. Thus, pressure valve 160 opens when the pressure within water seal chamber 14g exceeds a predetermined positive pressure, for example, on the order of 1-2 cms H₂O. Backflow of atmospheric air through the valve into the water seal container is prevented. While not illustrated, it will be appreciated that this valve can be located in the header above the water seal in container 14g.

In FIG. 21, there is illustrated a water seal container 14h which is secured to manifold Mh. Conduit 36h extends through manifold Mh providing communication between water seal container 14h and the suction control container, not shown. Tube 80h is adapted for connection to the vacuum source, also not shown in this Figure. Water seal tube 44h includes a tube or conduit 170 in communication with the collection chambers and having one or more circumferentially spaced openings 172 over which an elastomeric sleeve 174 is positioned. When pressures in excess of the predetermined positive pressure obtain in the collection containers, this pressure forces sleeve 174 to yield and become spaced from tube 170 to vent the containers and thereby prevent positive pressures beyond a predetermined pressure.

To prevent loss of suction control water in suction control container 12, in the event of a predetermined positive pressure in the system, the lower end of suction control tube 62j may be bevelled and provided with a flap valve 180 (see FIG. 22). With negative pressure within the system, atmospheric air flows unrestricted past flap valve 180 and into the air chamber within the suction control container provided the negative pressure exceeds the height of the water column above the lower end of suction control tube 62j. If the system pressure becomes positive instead of negative, the flap 180 seals tube 62j preventing egress of water through the tube o ut of the suction control container. This avoids loss of suction control water and consequent loss of suction control. Flap valve 180 is preferably utilized in conjunction with the anti-positive pressure check valve illustrated in FIGS. 20 and 21 respectively A bleed vent may be provided in flap 180 to enable siphoning of suction control water from the suction control contained This may be necessary in the event of changes in the patient's condition. This bleed vent is sufficiently small to preclude escape of suction control water up the suction control tube during transient periods of positive pressure but sufficiently large to enable siphoning from the suction control container.

It will be appreciated that high negative pressure in the collection containers and pleural cavity can also occur due to transient over-evacuation of the system by improper vacuum source settings or partial obstructions in the interconnecting passages. Water seal water could be lost by siphoning through the water seal tube into the collection containers. To avoid this and referring to FIG. 23, there is provided an anti-high negative pressure check valve at the lower end of water seal tube 44k. The lower end of tube 44k is bevelled and a flap 190 having a small vent opening 192 is provided. Consequently, if the pressure in the collection containers and the patient's pleural cavity exceeds a predetermined negative pressure, valve 190 seals the opening in tube 44k, except for the bleed vent 192, preventing the water in the water seal container from being siphoned into the collection containers. It will be appreciated that other appropriate types of check valves, i.e. ball or flutter type check valves, affording substantially unrestricted ingress into the water seal container from the collection container and limited or no egress from the water seal container to the collection containers would be suitable.

Figure 24:
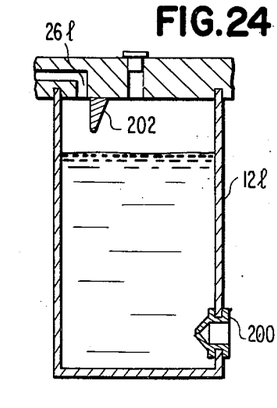
FIG. 24 is a vertical cross-sectional view of a suction control container constructed in accordance with a still further form of the present invention.

FIG. 24 illustrates a suction control container 12-1 having a check valve 200 located adjacent the lower end of the container at an elevation corresponding to the elevation of the lower ends of the suction control tubes previously discussed. Check valve 200 permits air to enter the container in response to system pressures in excess of the height of water above valve 200 but prevents the water from exiting the container. Thus, check valve 200 controls the system vacuum similarly as the suction control tube of the previous embodiments. Container 12-1 is also provided with a downwardly projecting splash shield 202 adjacent the passage 26-1 communicating between the suction control air chamber and the water seal container, not shown in this Figure. The splash shield minimizes water loss due to entrainment or evaporation. This embodiment has the advantage that the suction control tube and flap type check valve, for example of the embodiment of FIG. 22, can be replaced by a simple check valve. Also it facilitates adjustment of the water level which can be accomplished simply by forcing the check valve open to permit drainage.

Figures 23, 25, 26:
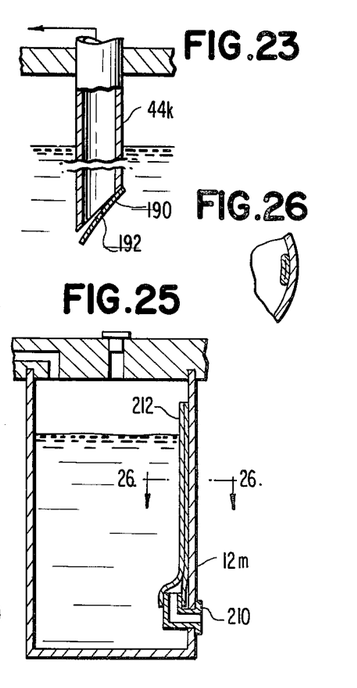
FIG. 25 is a view similar to FIG. 24 illustrating a still further embodiment of a suction control chamber constructed in accordance with the present invention.
FIG. 26 is a cross-sectional view thereof taken generally about on line 26—26 in FIG. 25.

In FIGS. 25 and 26, a still further form of suction control apparatus is illustrated. In this form, the rigid suction control tube 62 is replaced by an elbow fitting 210 formed in the side of the suction control container 12m. A flat flexible tube 212 extends upwardly from fitting 210 and terminates at an elevation above the level of liquid in suction control container 12m. The tube 212 may be suitably affixed to the interior wall of container 12m along its length or at its top, for example by an adhesive or a mechanical fixture. Tube 212 may be formed of a suitable rubber or flexible film material that is capable of sealing and opening under small pressure differentials on the order of 0.5 to 1 inches of $H_2O$.

Flexible tube 212 lays flat and remains sealed as illustrated particularly in FIG. 26 until the negative pressure in air chamber above the liquid level in the suction control container exceeds the height of the water column to the fitting 210. At that time, atmospheric air is admitted through fitting 210 and through flexible tube 212. As in the embodiment of FIGS. 1-9, there is no air entrainment of water since there is no air-water contact until the air flows into the air chamber above the liquid level in the suction control container. Thus, loss of suction control water is minimized. Also, air passing through tube 212 vibrates the wall of tube 212 providing visual indication that the vacuum control system is operative and that the vacuum is at the correct predetermined level.

Figure 27:
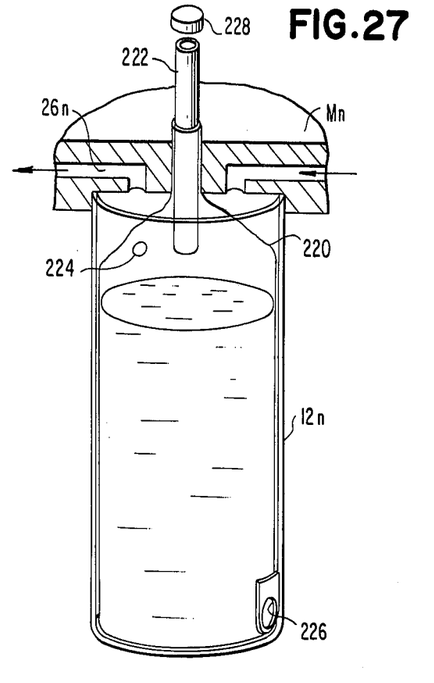
FIG. 27 is a fragmentary perspective view with parts broken out and in cross-section of a further form of suction control container constructed in accordance with the present invention.

Referring now to the embodiment hereof illustrated in FIG. 27, another form of suction control is disclosed. In this form, spillage, air entrainment, and evaporation of suction control water is prevented. Particularly, suction control container 12n is attached to manifold Mn and lies in communication with the water seal container, not shown in this Figure, by a passage 26n. Disposed within container 12n is a flexible bag or container, the upper end of which receives and is suitably secured to a filler tube 222. Bag 220 may be hermetically sealed about tube 222 but may have a small opening 224 above the level of the liquid within the bag.

At the lower end of container 12n, there is provided an opening 226 providing communication into container 12n exteriorly of bag 220. It will be appreciated that bag 220 substantially fills container 12n such that when the negative pressure within the system is at or less than the predetermined negative pressure, the bag 220 and pressure developed by the water therein seals opening 226 from the air chamber above bag 220 and within container 12n. When the pressure exceeds the predetermined negative pressure, atmospheric air displaces the wall of the bag inwardly and pulsates upwardly between the bag and container walls for communication with the air space above bag 220 within container 12n. A check valve may be provided in opening 226 if desired whereby air is permitted to enter container 12n but prevented from exiting therefrom.

Flexible bag 220 may be formed of a pair of opposed thin flexible sheets heat sealed along their sides and bottom and gathered at the top about filler tube 222. Tube 222 is provided with a cap 228 which seals its upper end when the bag is filled with the water to the desired level. Consequently, air ingresses into container 12n to control the suction in the system without entrainment or evaporation of water. Also, water from the suction control container cannot be spilled in the absence of puncturing the bag 220.

Figure 28:
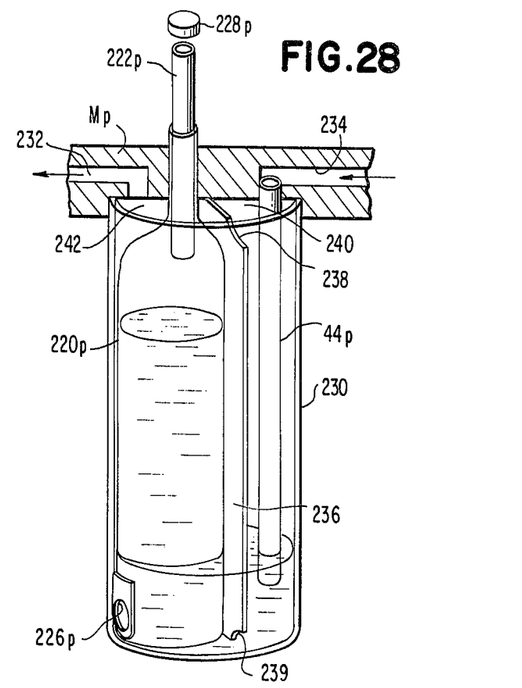
FIG. 28 is a view similar to FIG. 27 illustrating a combination water seal and suction control container.

Referring now to FIG. 28, there is illustrated another form of suction control device for the drainage system hereof whereby spillage, air entrainment and evaporation of suction control water is prevented. In this form, there is provided a combination water seal and suction control container 230 connected to manifold Mp. In this form, container 230 communicates with a vacuum source through passage 232 in manifold Mp and collection containers, not shown in this Figure, through passage 234. Container 230 is partitioned by a wall 236 which is inset at its upper and lower ends at 238 and 239 respectively, to provide for air and water communication between the chambers 240 and 242 formed by wall 236 and container 230. A flexible bag 220p containing suction control water, and construction similarly as bag 220 of the previous embodiment, is disposed within chamber 242 on one side of partition 236. Bag 220p is closed at its upper end by a filler tube 222p and cap 228p. An opening 226p is provided through the wall of container 230 adjacent its lower end for communication with chamber 242 but which opening is sealed by bag 220p in like manner as discussed above with respect to the embodiment of FIG. 27. The opening is provided with a check valve.

A water seal tube 44p depends from manifold Mp and lies in communication with passage 234. The lower end of tube 44p extends below the water level within container 230 external to water bag 220p.

The operation of this form of the invention is believed evident from the description of the operation of the embodiments of FIGS. 1-9 and 27, the difference here being the consolidation of the water seal and suction control functions in a single container secured to the manifold. It will be evident that when the desired negative pressure within the system is exceeded, atmospheric air enters container 230 through opening 226p and passes upwardly between the walls of containers 230 and bag 220 into the space above bag 220p. The air then passes into chamber 240 through the inset openings 238 in partition 236. It will be appreciated that the compartments 240 and 242 may be sealed at their lower ends with water for the water seal provided only in water seal compartment 240.

Figures 29, 30:
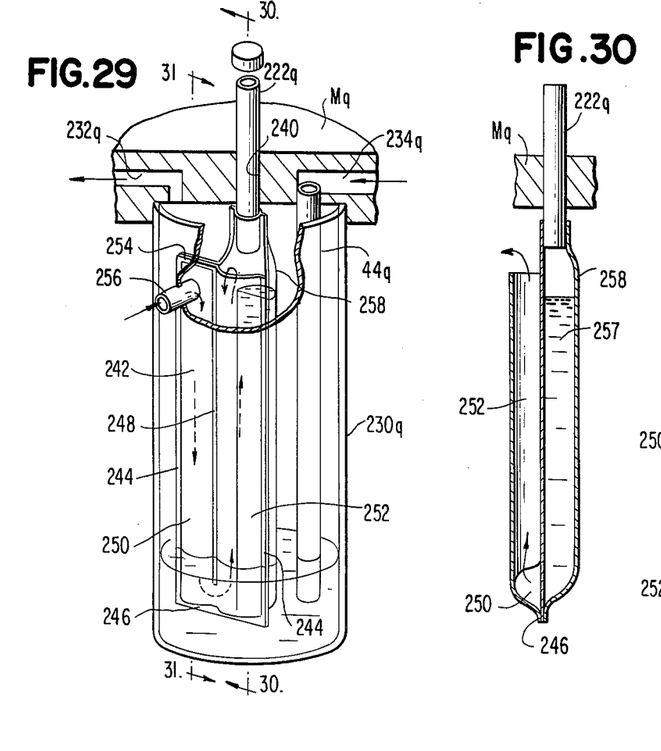
FIG. 29 is a view similar to FIG. 28 illustrating a still further form of a combination water seal and suction control container constructed in accordance with the present invention.
FIGS. 30 and 31 are cross-sectional views thereof taken generally about on lines 30—30 and 31—31, respectively in FIG. 29.

Referring now to the embodiment hereof illustrated in FIG. 29, there is illustrated a combined water seal and suction control container 230q secured to the underside of a manifold Mq. Manifold Mq contains a passage 232q in communication with the container 230q and a vacuum source, a passage 234q communicating with collection containers, not shown in this Figure, a depending water seal tube 44q and an opening 240 for receiving a filler tube 22q.

Within container 230q, there is disposed a dual column air sleeve 242 formed preferably by heat sealing a pair of film sheets along their side and bottom margins 244 and 246 respectively. The opposed films are also heat sealed one to the other along a vertical line indicated 248 intermediate side margins 244, this intermediate seal extending from the top of sleeve 242 to an elevation spaced above the bottom margin seal 246 whereby discrete air channels 250 and 252 are formed which lie in communication one with the other at the bottom of the dual column air sleeve 242. Channel 250 is closed at its top by heat sealing the top portion of the opposed films at 254. The top of the opposed films forming channel 252 are left open. A nipple 256 is provided through the wall of container 230q in communication with the upper end of channel 250 whereby air may enter the dual column sleeve through nipple 256, pass downwardly along channel 250 and then upwardly along channel 252 into the air space adjacent the top of container 230q.

A third film 258 is preferably similarly heat sealed along one side margin 244, intermediate seam 248, and bottom seam 246 to form a third channel of column 257. Column 257 receives water through filler tube 222q which is received within the top of column 257 between film 258 and the intermediate film forming the interior side of the air channel 252. The water received in column 257 is thus contained thereby by the plastic film.

In use, container 230q is provided with a level of water just above the lower end of water seal tube 44q. Passage 232q is also coupled to a vacuum source, not shown. Column 257 is filled with water to an appropriate level corresponding to the desired negative pressure rquired in the system. When the negative pressure in the system is equal to or less than the predetermined negative pressure, the intermediate film forming the interior side of air channel 252, bears against the opposed film to seal air channel 252 under the pressure of the water in column 257 whereby air is prevented from entering the air chamber in container 230q through the dual column air sleeve 242. When the negative pressure in the system exceeds the desired negative pressure, the air pulsates upwardly from the bottom of air channel 253 between the plastic films into the air space above the water in container 230q. Thus the vacuum level in the system is maintained at a predetermined level. When the air pulsates upwardly through channel 252, the film material undulates whereby a visual indication that the system is working properly is provided. As in the prior embodiment, spillage, air entrainment and evaporation of the suction control water is precluded.

Figure 32:
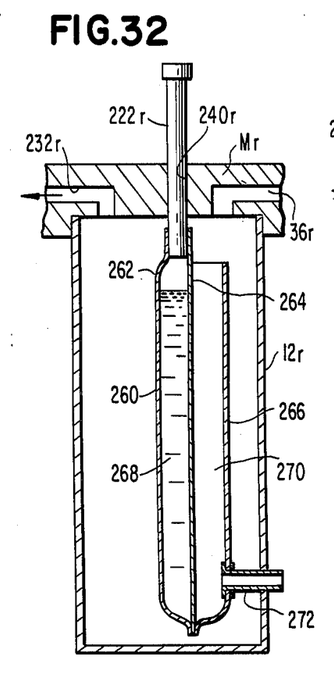
FIG. 32 is a fragmentary vertical cross-sectional view of a suction control container constructed in accordance with a still further embodiment of the present invention.

Referring now to FIG. 32, there is provided a suction control container 12r secured to a manifold Mr having a passage 232r in communication with a vacuum source and a passage 36r in communication with a water seal container, not shown in this Figure. Manifold Mr also has an opening 240r for receiving a filler tube 222r in communication at its lower end with a dual air and water column sleeve 260. Sleeve 260 is formed by heat sealing three facing plastic films 262, 264 and 266 along their side and bottom margins thereby defining a water column 268 between films 262 and 264 and an air column 270 between films 264 and 266. Air column 270 is open at its top between walls 264 and 266. At the lower end of air column 270 there is provided a nipple 272 which extends through the side wall of container 12r.

In use, when the negative pressure within the system is equal to or less than the predetermined negative pressure, the intermediate film 264 under the force of the water pressure within the water column 268 seals against outer film 266 closing air column 270 whereby air cannot enter the suction control container 12r by way of nipple 272. When the negative pressure within the system exceeds the desired negative pressure, air enters nipple 272 and pulsates upwardly through the air column 270. Thus, as in the prior embodiment, the air entering the system provides a visual indication that the system is working properly by fluttering the plastic film 266.

Figure 31:
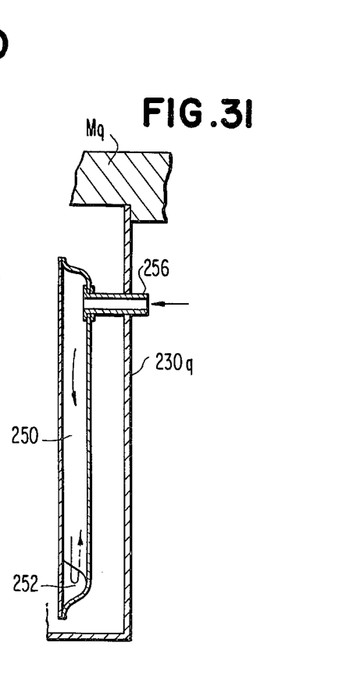

It will be appreciated that the container 12r illustrated in FIG. 32 may also comprise a combined water seal and suction control container similarly as in the embodiment illustrated in FIGS. 29–3, the dual water and air column of FIG. 32 being substituted for the dual column of FIGS. 29–31.

Figure 33:
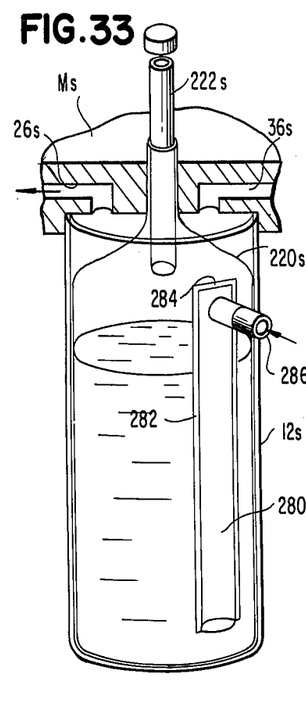
FIGS. 33–36 are views similar to FIG. 32 illustrating respective further embodiments of suction control containers constructed in accordance with the present invention.

Referring now to the embodiment hereof illustrated in FIG. 33, there is illustrated a further form of suction control container similar to the suction control container illustrated in FIG. 27. In this form, a manifold Ms is provided having a passage 26s in communication between a vacuum source, not shown, and suction control container 12s secured to manifold Ms. Manifold Ms also has a passage 36a in communication between a water seal container, not shown in this Figure, and the suction control container 125. As in the embodiment of FIG. 27, manifold Ms is provided with opening for receiving a filler tube 222s about which the upper end of a flexible bag 220s is secured, bag 220s being disposed within suction control container 12s. A flexible air sleeve 280 formed preferably by heat sealing a pair of thin plastic films together along their side and top margins at 282 and 284 respectively is disposed along the inside wall of container 12s between it and bag 220s. The lower end or air sleeve 280 is open.

In operation, when the vacuum pressure within the system is equal to or less than the desired negative pressure, the water pressure within bag 220s bears and seals the opposite walls of the air column 280 against one another to prevent ingress of air into the container 12s through nipple 286. When the negative pressure in the system exceeds the desired negative pressure, atmospheric air flows into the air chamber defined above bag 220s through the nipple 286 and sleeve 280 and exits at the bottom of the sleeve to pulsate upwardly between the walls 12s and the container 220s into the air chamber above bag 220s. The arrangement of this embodiment not only prevents spillage, air entrainment and evaporation of suction control water but enables continued operation even in the event bag 220s is punctured or breaks.

Figure 34:
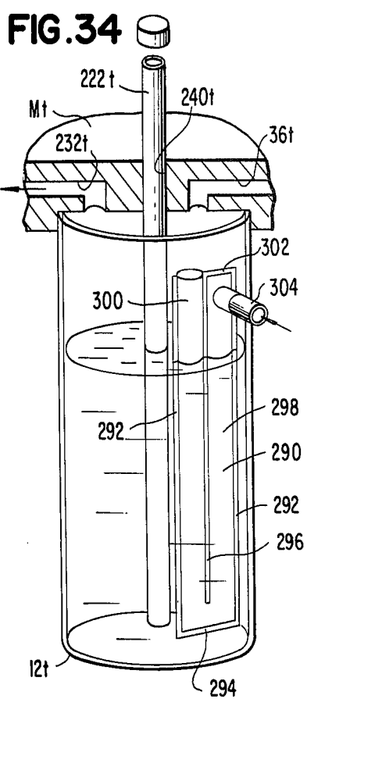

Referring now to the embodiment hereof illustrated in FIG. 34, there is illustrated a suction control container 12t secured to a manifold Mt having a passage 232t in communication between a vacuum source and suction control container 12t. Manifold Mt also has a passage 36t in communication between a water seal container, not shown in this Figure and suction control container 12t. Manifold Mt also has an opening 240t for receiving a filler tube 222t for filling the suction control container 12t to the appropriate level.

A dual air column sleeve 290 is provided in suction control container 12t. The dual air column sleeve 290 is preferably formed by heat sealing a pair of plastic, thin film, sheets along their side and bottom margins at 292 and 294 respectively. The opposed films are also heat sealed one to the other along a vertical line indicated 296, intermediate side margins 292. This intermediate seal extends from the top of sleeve 290 to an elevation spaced slightly above the bottom margin seal 294 whereby discrete air channels 298 and 300 are formed and which channels lie in communication one with the other at the bottom of the dual column air sleeve 290.

Channel 298 is closed at its top by heat sealing the upper margin of the opposed films at 302. The top of the opposed films forming channel 300 are left open. A nipple 304 is provided through the wall of container 12t in communication with the upper end of channel 298 whereby air may enter the dual column sleeve through nipple 304, pass downwardly along channel 298, and then upwardly along channel 300 into the air space above the water level in suction control container 12t.

When negative pressure in the system is equal to or less than the predetermined negative pressure, the water pressure within container 12t forces the opposite sides of the films forming the air channels 298 and 300 toward one another to seal the air channels defined therebetween whereby air is prevented from entering the air chamber in the suction control container 12t. When the negative pressure in the system exceeds the desired negative pressure, air enters nipple 304, passes downwardly along channel 298 and then upwardly along channel 300 into the space above the water in suction control container 12t. Thus, the vacuum level in the system is maintained at a predetermined level without spillage, air entrainment, or evaporation of the suction control water. The flexible dual column sleeve also undulates when air passes through it to provide a visual indication that the system is working properly.

Figure 35:
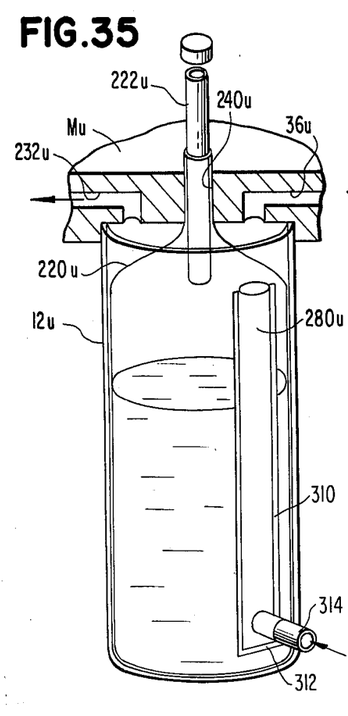

Referring now to FIG. 35, there is illustrated another form of suction control container 12u secured to manifold Mu. Manifold Mu has a passage 232u in communication between a vacuum source and suction control container 12u. Manifold Mu also has passage 36u in communication between a water seal container, not shown in this Figure and suction control container 12u. Manifold Mu also has an opening 240u for receiving a filler tube 222u, about the lower end of which is gathered and secured a flexible bag or container 220u for containing suction control water disposed therein to the desired level. A flexible air sleeve 280u, formed preferably by heat sealing a pair of thin plastic films together along their side and bottom margins at 310 and 312 respectively, is disposed along the inside wall of container 12u between it and bag 220u. The upper end of the air sleeve 280u is open and its bottom end lies in communication with a nipple 314 extending through the wall of suction control container 12u.

In operation, when the vacuum pressure within the system is equal to or less than the desired negative pressure, the water pressure within bag 220u bears against and seals the opposite walls of the air column 280u to one another to prevent ingress of air into container 12u through nipple 314. When the negative pressure in the system exceeds the desired negative pressure, atmospheric air flows into the air chamber defined at the upper end of container 12u between it and bag 220 through the nipple 314 and the air column 280. As in previous forms, the air column may be adhesively secured to the wall of the container 12u if desired. This arrangement also prevents slippage, air entrainment and evaporation of suction control water and enables continued operation even in the event bag 220u is punctured or breaks.

Figure 36:
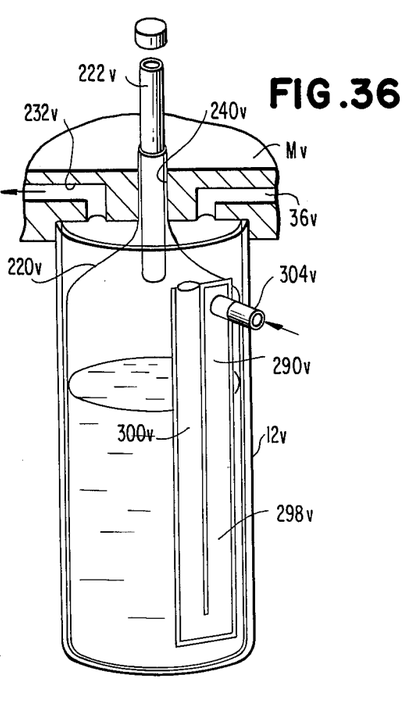

Referring now to the final embodiment disclosed in this application in FIG. 36, there is illustrated a suction control container 12v carrying a container or bag 220v which is gathered and sealed about the lower end of filler tube 222v. Filler tube 222v extends through an opening 240v formed in manifold Mt. Manifold Mv has a passage 232v in communication between a vacuum source, not shown, and suction control container 12v. Manifold Mv also has a passage 36v in communication between the water seal container not shown in this Figure and the suction control container 12v. There is also provided a dual column air sleeve 290v which is similar in all respects to the dual column air sleeve 290 illustrated in FIG. 34. Thus, the suction control container of this embodiment is, in effect, the dual column air sleeve disclosed in FIG. 34 combined with the bag 222u disclosed in FIG. 35.

In operation, when the vacuum pressure within the system is equal to or less than the desired negative pressure, the water pressure within bag 220v bears against and seals the opposite walls of the dual column air sleeve 290v to one another to prevent ingress of air into the container 12v through nipple 304v. When the negative pressure in the system exceeds the desired negative pressure, the atmospheric air flows into the air chamber above bag 220v through nipple 304v, along channel 298v and 300v. Visual indication of proper system operation is provided by the fluttering action of the sleeve.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A suction control apparatus comprising:
    a suction control container adapted to receive a predetermined quantity of liquid thereby defining an air chamber above the level of liquid therein, said air chamber being in fluid communication with a vacuum source; and
    a passage for communicating atmospheric air external to said apparatus into said suction control container to a location below the level of liquid in said container, said air flowing from said location into said air chamber of said suction control container for controlling the negative pressure of said vacuum source; said passage including means for reducing the loss of liquid from said suction control container due to liquid entrainment in the air flowing through the container and for attenuating noise in said suction control apparatus, said latter means including means for transmitting said atmospheric air into said air chamber without contact with the liquid in the suction control container during said transmission of air.

2. Apparatus according to claim 1 wherein said means for reducing the loss of liquid and for attenuating noise in said suction control apparatus includes an air inlet in said suction control container at the predetermined distance below the level of liquid in said container; and a flexible sleeve open at opposite ends, having one end in communication with said inlet and the opposite end extending above the level of liquid in said container for transmitting atmospheric air from said inlet into the air chamber without contact with the liquid in the suction control container during said transmission of air.

3. Apparatus according to claim 1 wherein said means for transmitting includes a tube extending into said suction control container to a point below the level of liquid in said suction control container.

4. Apparatus according to claim 3 wherein said transmitting means includes a sleeve lying in communication with said lower tube end and having an open end located in said air chamber.

5. Apparatus according to claim 4 wherein said sleeve is formed of a flexible material, said sleeve being responsive to a negative pressure within said suction control container equal to or less than a predetermined negative pressure to seal said passage and responsive to a negative pressure within said suction control container above said predetermined negative pressure for opening said passage.

6. Apparatus according to claim 5 wherein said sleeve is elongated and envelops at least a portion of said tube, said sleeve being closed at its lower end for defining an air passageway from said lower tube end to said chamber.

7. Apparatus according to claim 6 including means carried by said tube for spacing the closed lower end of said sleeve from said lower tube end.

8. Apparatus according to claim 7 including means for securing said sleeve to said tube.

9. Apparatus according to claim 6 wherein said sleeve has a first compartment for receiving at least a portion of said tube and a second compartment in communication with said first compartment adjacent the lower end of said sleeve for transmitting air from said tube directly into said air chamber.

10. Apparatus according to claim 9 wherein said sleeve has a third compartment in communication with said first compartment adjacent the lower end of said sleeve for transmitting air from said tube directly into said air chamber.

11. Apparatus according to claim 1 wherein said apparatus also includes an alternative passage for communicating atmospheric air external to said apparatus into said suction control container for egress therein at a location below the level of liquid within said suction control container for bubbling through the liquid into said air chamber, and means for selectively blocking one of said passages for communicating atmospheric air into said air chamber through either of said passages.

12. Apparatus according to claim 11 wherein said alternative passage is defined by a tube extending into said suction control container, one end of said tube lying at a like elevation in said suction control container as said location.

13. Apparatus according to claim 1 wherein said means for transmitting includes a flexible container disposed within said suction control container, said predetermined quantity of liquid being confined within said flexible container and said air chamber being defined above the level of liquid in said flexible container, said passage including a passageway extending between the walls of said suction control container and said flexible container, a portion of said passageway being located a predetermined distance below the level of liquid in said flexible container, said flexible container and the liquid therein for sealing said passageway in response to a negative pressure in said air chamber equal to or less than a predetermined negative pressure.

14. Apparatus according to claim 13 wherein said flexible container with the liquid therein substantially fills the lower portion of said suction control container, said suction control container including an opening through its side wall at said predetermined distance below the level of liquid in said flexible container said opening lying in communication with said passageway.

15. Apparatus according to claim 14 including a check valve in said opening.

16. Apparatus according to claim 13 including a flexible sleeve forming a part of said passageway, said sleeve extending between the walls of said flexible container and said suction control container.

17. Apparatus according to claim 16 wherein said sleeve has one end thereof disposed above the level of liquid in said flexible container, and said apparatus includes means for communicating between said sleeve and the atmospheric air external to said apparatus, the opposite end of said sleeve being open and disposed at said predetermined distance below the level of liquid in said flexible container.

18. Apparatus according to claim 16 wherein said sleeve has one end thereof disposed at said predetermined distance below the level of liquid in said flexible container, and said apparatus includes means for communicating between said one sleeve end and atmospheric air external to said apparatus, the opposite end of said sleeve being open and disposed above the level of liquid in said flexible container.

19. Apparatus according to claim 16 wherein said sleeve is divided into first and second air channels, said sleeve having one end of each of said first and second air channels disposed above the level of liquid in said flexible container with the opposite ends of said first and second air channels being disposed at said predetermined distance below the level of liquid in said flexible container, and in communication one with the other, and said passage includes means for communicating between the one end of said first channel and atmospheric air external to said apparatus, the one end of said first channel being open.

20. Apparatus according to claim 1 wherein said means for transmitting includes a flexible sleeve in said suction control container defining first and second channels, said first channel being closed at its lower end and adapted to receive a predetermined quantity of fluid forming a fluid head, means for communicating atmospheric air into said second channel with said second channel defining an air passageway into said suction control container substantially coextensive with the fluid head provided by said first channel whereby said flexible sleeve and the fluid in said first channel seal the air passageway through said second channel in response to a negative pressure in said suction control container equal to or less than a predetermined negative pressure and enable atmospheric air to flow through said second channel into said suction control container in response to a negative pressure in said suction control container above said predetermined negative pressure.

21. Apparatus according to claim 20 wherein said second channel is divided into first and second air passageways with one end of each passageway disposed above the fluid level in said first channel and their opposite ends disposed adjacent the lower end of said first channel and in communication one with the other, means providing for communication between the one end of said first passageway and atmospheric air external to said apparatus.

* * * * *